(12) United States Patent
Davis et al.

(10) Patent No.: US 7,383,183 B1
(45) Date of Patent: Jun. 3, 2008

(54) METHODS AND SYSTEMS FOR PROTECTING PRIVATE INFORMATION DURING TRANSCRIPTION

(75) Inventors: Tad Alan Davis, Morgantown, WV (US); Howard S. Hoffmann, New Rochelle, NY (US); Emmy Brock Weber, Marietta, GA (US); Mark Ivie, Moorestown, NJ (US); Dori Dunn, Surprise, AZ (US); Vasudevan Jagannathan, Morgantown, WV (US)

(73) Assignee: Medquist Inc., Mount Laurel, NJ (US)

( * ) Notice: Subject to any disclaimer, the term of this patent is extended or adjusted under 35 U.S.C. 154(b) by 0 days.

(21) Appl. No.: 11/860,902

(22) Filed: Sep. 25, 2007

(51) Int. Cl.
*G10L 15/00* (2006.01)
*G06Q 10/00* (2006.01)

(52) U.S. Cl. .................. 704/235; 704/270; 704/275; 705/2; 705/3

(58) Field of Classification Search ............ 704/235, 704/270, 275; 705/2, 3
See application file for complete search history.

(56) References Cited

U.S. PATENT DOCUMENTS

| | | | |
|---|---|---|---|
| 5,956,298 A | 9/1999 | Gough | |
| 6,571,211 B1 | 5/2003 | Dwyer | |
| 6,874,085 B1 | 3/2005 | Koo | |
| 7,006,999 B1* | 2/2006 | Huberman et al. | 705/74 |
| 2005/0065816 A1* | 3/2005 | Limberg et al. | 705/2 |
| 2005/0246205 A1* | 11/2005 | Wang et al. | 705/3 |
| 2006/0089857 A1 | 4/2006 | Zimmerman | |
| 2006/0190263 A1* | 8/2006 | Finke et al. | 704/270 |
| 2007/0081428 A1 | 4/2007 | Malhotra | |
| 2007/0265888 A1* | 11/2007 | Castelli | 705/4 |
| 2008/0033757 A1* | 2/2008 | Kozloff et al. | 705/2 |

* cited by examiner

*Primary Examiner*—Daniel D Abebe
(74) *Attorney, Agent, or Firm*—Buchanan Ingersoll & Rooney PC

(57) ABSTRACT

Systems and methods are disclosed for transcribing private information. The method, includes receiving a first information segment during a first interview session, and receiving a second information segment during a second interview session, wherein the first information segment A includes private information and the second information segment includes only non-private information. The exemplary method also includes providing information in the first information segment to a first transcriber, providing information in the second information segment to a second transcriber, wherein the second transcriber has no communication with the first transcriber. The exemplary method further includes providing a combination of the information transcribed from the first and second information segments to a user or other recipient authorized to receive the private information.

17 Claims, 3 Drawing Sheets

METHODS AND SYSTEMS FOR PROTECTING PRIVATE INFORMATION DURING TRANSCRIPTION

FIELD

The present disclosure relates generally to data transcription, and more particularly to methods and systems for transcribing dictation.

BACKGROUND

Transcription services translate verbal dictation into text documents. Typically, a user of a transcription service speaks information into a device to be stored as an audio file. When, for example, the user is a health care provider, the audio file can include patient-specific information such as the patient's name, age, and medical record number. The resulting dictation is given to a transcriptionist for translation into a text document. Because patient-specific information in the dictation is revealed to the transcriber, the transcription process places the patient's private information at risk of unauthorized disclosure.

Patient-specific information is referred to as protected health information (PHI). Protected health information generally includes health information that reasonably could be expected to allow identification of an individual. More specifically, protected health information is any information that identifies an individual, as well as the individual's relatives, employers, or household members. Protected health information can include, for example, names, addresses, dates (e.g., birth date, admission date, discharge date, date of death), contact information, medical record numbers, and account numbers.

Good medical practice requires that patients' private information be protected from disclosure or use without consent. Health care providers may also be liable under privacy laws, such as The Health Insurance Portability and Accountability Act of 1996, for unauthorized disclosure of protected health information.

Some prior patent references attempt to protect information during the transcription processes. For instance, U.S. Patent Application Publication No. 2007/0081428 to Malhotra et al. discloses a transcription system in which private information is filtered from dictation so that transcriptionists never have access to the private information. A software program extracts any private information and, after the transcription is completed, reinserts the removed private information back into the final report.

The disclosed methods and systems for information transcription are directed toward, but not limited to, improving the above-noted methods for transcribing medical dictation.

SUMMARY

Exemplary embodiments disclosed herein provide methods and systems for transcribing private information. The method, for example, includes receiving a first information segment during a first interview session, and receiving a second information segment during a second interview session, wherein the first information segment includes private information and the second information segment includes only non-private information. The exemplary method also includes providing the information in the first information segment to a first transcriber, and providing the information in the second information segment to a second transcriber, wherein the first transcriber and the second transcriber do not communicate information from the first segment or the second segment to one another. The exemplary method further includes providing a combination of the information transcribed from the first and second information segments to a user or other recipient authorized to receive the private information.

DETAILED DESCRIPTION

Figure 1:
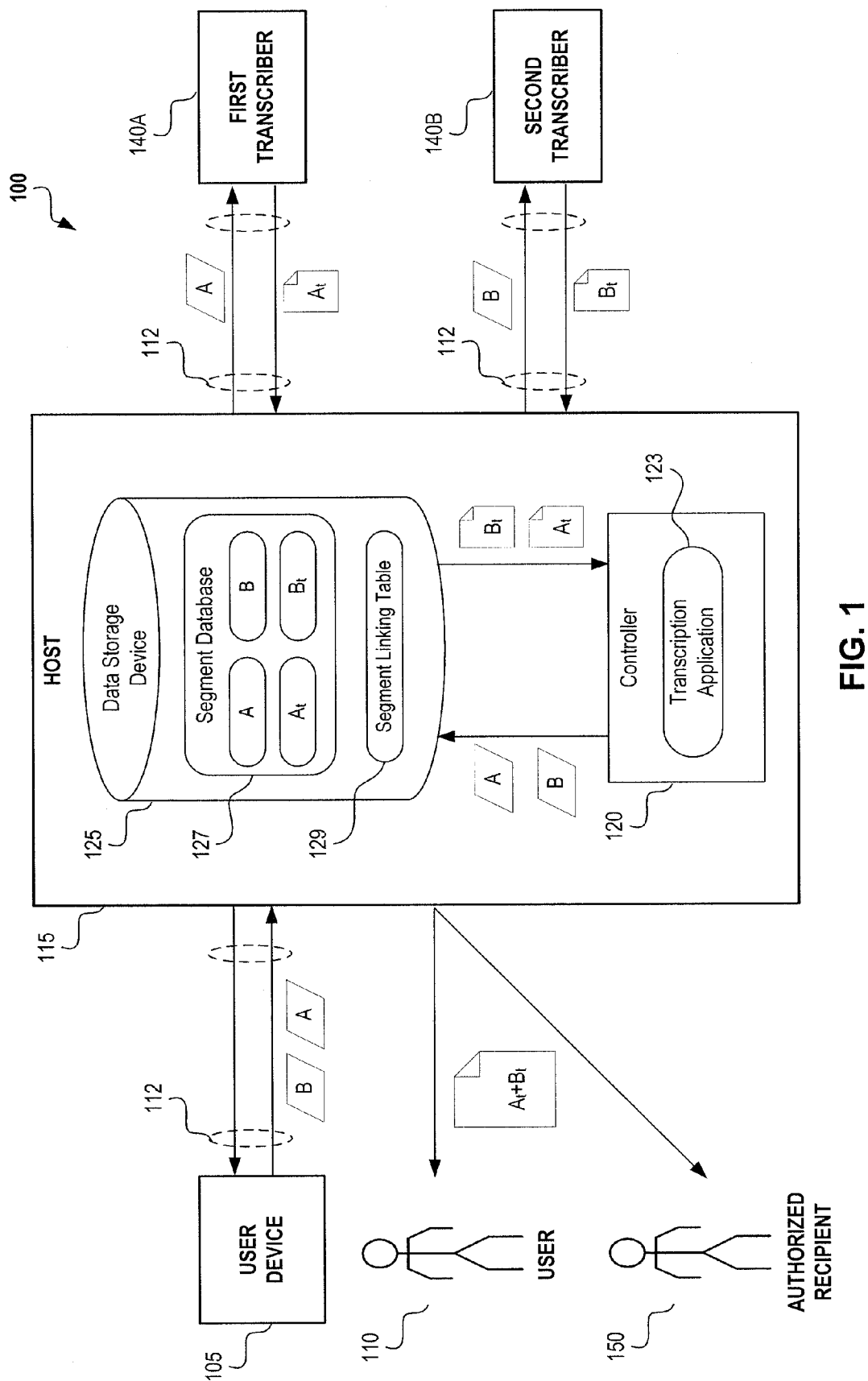
FIG. 1 is a block diagram illustrating an exemplary system as disclosed herein.

FIG. 1 is a block diagram illustrating a system environment 100 for a transcription system that is consistent with some exemplary embodiments. In system environment 100, a host (e.g., host 115) receives information from a user (e.g., user 110) in separate segments (e.g., information segments A & B), provides the segments to different transcribers (e.g., transcribers 140A & 140B), retrieves the corresponding translated segments (e.g., documents $A_t$ & $B_t$), and provides the translated information segments to the user or another recipient (e.g., recipient 150) authorized to access the private information.

Private information is any information that should not be accessed by anyone who is not authorized. Private information can be information that is secret, confidential, protected, proprietary, or identifies an individual. Non-private information is any information that is not private information, such as information that is de-identified (i.e. information that is not associated with any identifying information), public knowledge, unprotected, or generalized such that it does not identify an individual.

An exemplary system environment 100 can include a transcription system that receives dictation from a health care provider in separate segments, transcribes the segments into text, generates a document including the transcribed text for each segment, and provides the document to the health care provider or other entity authorized by the patient to receive the patient's protected health information. Although exemplified in the context of transcription of medical data, any environment consistent with the present disclosure may benefit from the disclosed methods or systems.

As shown in FIG. 1, exemplary system environment 100 can include a user device 105, a user 110, a host 115, a first transcriber 140A, a second transcriber 140B, and a recipient 150. User device 105 can be a device or system for receiving and/or recording information segments A & B from user 110, and for communicating the information segments to host 115 for transcription.

User 110 is any individual that desires to have dictation transcribed. For instance, user 110 can be a health care provider, a lawyer, an insurance agent or a respective staff member who may desire to have dictation translated into text. User device 105 can be any device for capturing information from user 110, such as a dictation machine, a telephone, a personal computer (e.g., desktop or laptop), a handheld recording device, a smart phone, or a personal digital assistant. User device 105 also can be a special purpose device that allows user 110 to dictate, store, and access audio and or audiovisual files for transmission to host 115.

User device 105 can include one or more memory devices for temporary, semi-permanent and/or permanent storage of information segments. Memory device can include, for instance, magnetic tapes, magnetic discs, semiconductor-based memories (e.g., random access memory, or flash memory). Information recorded by user device 105 can be audio data, audiovisual data, text data, or combinations thereof. Information segments can be recorded in analog or digital formats which may or may not compress or encrypt the data.

User device 105 can also have various input devices. For receiving user 110's dictation, user device can include a regular phone, a microphone or some other sound transducer configured to record speech, and/or an interface for receiving an audio file from a portable recording device. Other input devices can receive user-inputs for controlling software applications, graphical user interfaces and/or other programs; for example, a keyboard, switch, a slide, a trackball, a touch-screen, a joystick, or other such devices. User device 105 also can have output devices for prompting user 110 for information (e.g., information segments A & B), such as loudspeakers, displays (e.g., computer display) and indicators (e.g., flashing lights).

User device 105 can also include a communication interface (not shown) for communicating information segments A & B to host 115 over communication channel 112. The communication interface can be, for instance, an analog, a serial, a parallel or a network interface. Via the communication interface, user device 105 can provide information segments A & B directly to host 115 as the information is recorded from user 110. Alternatively, information segments A & B can be stored as complete data files before being communicated to host 115. Furthermore, communication interface can secure information segments A & B using encryption (e.g., secure socket layer, or public-private key).

User device 105 can provide two separate information segments A & B to host 115. Information segments A & B are recorded and processed separately up to the point where they are combined for distribution to user 110 or some other authorized recipient 150 (e.g., a patient's health care provider).

Information segment A is a data file that can include private information, such as protected health information. In some exemplary embodiments, information segment A can be information describing content in information segment B. For instance, when dictating a medical report, a health care provider can provide header information in information segment A, which includes protected health information that describes the body of the report included in information segment B, which is generalized and/or de-identified such that it does not include protected health information.

Information segment A can be a structured data file. Structured data is information organized in fixed fields within a record or file, such as records in relational databases and entries in spreadsheets. When, for example, information segment A is an audio file, first information segment A can be a predetermined set of data that is provided in a particular order and stored in a structured data file having a predefined order of information portions. Host 115 can, for example, prompt user 110 to answer a particular series of questions, the responses to which can be tagged with identifying information and stored in a structured data file (or at least referenced in a structured manner). When first information segment is a text file, data for information segment A can be entered into a form presented on a graphical user interface having predetermined fields corresponding to the information to be included in information segment A. The fields of the structured data in information segment A can be used to populate records of a relational database.

Alternatively, first information segment A can be unstructured. For instance, user 110 can dictate or type the information segment in no particular order. A transcriber, such as transcriber 140A, can later translate the data and/or correlate the data with predetermined types, classes or fields for entry into a database record.

Information segment B is a data file that does not include private information. Second information segment B can be a non-structured data file that is spoken or typed by user 110. For instance, second information segment B can be a health care provider's narrative report describing of the details of a diagnosis or procedure to be included in the body of a letter or a report.

As further shown in FIG. 1, communication channel 112 connects host 115 with user 105 and/or transcribers 140. In some embodiments, communications channel 112 can be direct link, such as an analog, a serial or a parallel interface. In other embodiments, communication channel 112 can be a shared, public, private, or peer-to-peer network, encompassing any wide or local area network, such as an extranet, an intranet, the Internet, a Local Area Network (LAN), a Wide Area Network (WAN), a virtual private network (VPN), a voice over internet packet network (VoIP) a public switched telephone network (PSTN), an Integrated Services Digital Network (ISDN), or any other form of wired or wireless communication network that is appropriately secured to, for example, meet any regulatory requirements.

Further, communication channel 112 can be compatible with any type of communications protocol used by the components of system environment 100 to exchange data, such as the Ethernet protocol, ATM protocol, Transmission Control/Internet Protocol (TCP/IP), Hypertext Transfer Protocol (HTTP), Hypertext Transfer Protocol Secure (HTTPS), or peer-to-peer protocol. The particular composition and protocol of communication channel 112 is not critical as long as it allows for communication between host 115, user device 105 and/or transcribers 140.

Host 115 can be a device or system for receiving, storing, and/or processing information segments A & B provided from user device 105, and for providing the information segments to transcribers 140 for transcription. Host 115 can be implemented as one or more computer systems including, for example, a personal computer, minicomputer, microprocessor, workstation, mainframe, or similar computing platform.

Host 115 can include a controller 120 and data storage device 125. Controller 120 can include one or more microprocessors, computer readable memory (e.g., read-only memory (ROM), random access memory (RAM), mechanisms and structures for performing I/O operations. Controller 120 can execute an operating system for execution on the central processing unit and/or transcription application 123.

Data storage device 125 can store transcription application 123 that, when executed by controller 120, performs a method of transcribing information. Data storage device 125 can be implemented with a variety of components or subsystems including, for example, a magnetic disk drive, an optical disk drive, flash memory, or other devices capable of storing information.

Although controller 120 and data storage device 125 are shown as being within host 115, the location is merely exemplary. Controller 120 and data storage device 125 can be physically located inside or outside of host 115. For instance, data storage device 125 can be configured as a network accessible storage located remotely from controller 120.

As further shown in FIG. 1, data storage device 125 can include segment database 127 for storing information used by transcription application 123, including information segments A & B, translated information segments $A_t$ & $B_t$, and segment linking table 129. Segments A & B and translated segments $A_t$ & $B_t$ can be stored in a database by transcription application 123. Linking table 129 can be a table that stores information associating each A & B with $A_t$ & $B_t$, respectively.

Transcribers 140 can be individuals, software systems, or a combination thereof for translating dictation into text documents. Transcribers 140 can also include individuals who verify the accuracy of transcriptions performed by other individuals or computer programs that automatically perform speech-to-text translation. However, transcribers 140 are not necessarily limited to transcription of text and can perform other tasks, for instance, translating text from one format to another (e.g., ASCII to XML) or from one language to another.

Transcribers 140 can receive either one of separate information segments A & B from host 115, transcribe information segments A & B into text, and provide the transcribed information segments $A_t$ & $B_t$ to host 115 where they are stored, for example, in segment database 127 for later retrieval and combination by transcription application 125. To prevent disclosure of private information, transcriber 140A and transcriber 140B do not share information included in information segments A & B with one another. Information provided to transcribers 140 can also be de-identified with regard to the source of the data (e.g., the health care provider) to further minimize the risk of unauthorized disclosure. Transcribers 140 can by physically, functionally and/or operatively separated to prevent sharing or other communication of information included in information segments A & B. In some instances some de-identified information included in information segments A or B, such as gender and age range, may be shared with or between transcribers 140 to make transcription of the information more efficient.

In some embodiments, host 115 can provide information segments A & B to respective transcribers 140A & 140B using a streaming audio protocol. Streaming audio is a one-way audio transmission over a data network to audio on-demand. Audio that is streamed is played within a few seconds of requesting it, and the data is not stored at the transcribers' location (e.g., a remote terminal). As such, improper dissemination of segments A & B, including any private information, by transcribers 140 can be substantially prevented.

From translated information segments $A_t$ & $B_t$, and based on segment linking table 129, transcription application 123 can retrieve corresponding translated information segments. The combination of translated information segments $A_t$ & $B_t$ can then be provided to user 110 and other recipients 150 authorized to receive the private information included in the first information segment A. No human intervention is necessary to combine the translated information segments $A_t$ & $B_t$. As such, disclosure of private information is avoided.

Consistent with some exemplary embodiments, translated information in text file $A_t$ and translated information in text file $B_t$ can represent a header and a body portion of a report, respectively. Transcription application 123 can create a document by appending translated information segment $B_t$ to translated information segment $A_t$. Portions can be combined using a predefined manner that provides a document having a predetermined format.

As shown in FIG. 1, and consistent with the exemplary embodiments disclosed herein, the first information segment A (e.g., a header) and the second information segment B (e.g., a body) are recorded, received, transcribed and stored separately. Any private information is included in the first information segment A and no private information is included in the second information segment B. By keeping information segment A and information segment B separate, the exemplary embodiments can prevent the disclosure of private information to unauthorized individuals or systems.

Although information segment A (and corresponding translated information segment $A_t$) is disclosed as including private information and information segment B (and corresponding translated information segment $B_t$) is disclosed as excluding private information, the roles of information segments A and B can be reversed. Moreover, system environment 100 may include more than two segments. For instance, a third segment including information describing the source of the information (e.g., information identifying a health care provider) can be separately received by host 115 and/or stored in association with information segments A & B to prevent disclosure of the source of information segments A and/or B to transcribers 140. It should be understood that variations and numbers of segments may change so long as segments including private information are acquired and transcribed separately from segments that do not include private information.

Although user device 105, host 115, and transcribers 140 are shown in FIG. 1 as separate elements, some or all of them can be combined or divided into fewer or greater number of elements. The particular division of functions is for illustration only, and different elements may perform one or more of the tasks disclosed above, so long as first transcriber 140A and second transcriber 140B do not communicate or otherwise share information segment with one another.

Figure 2:
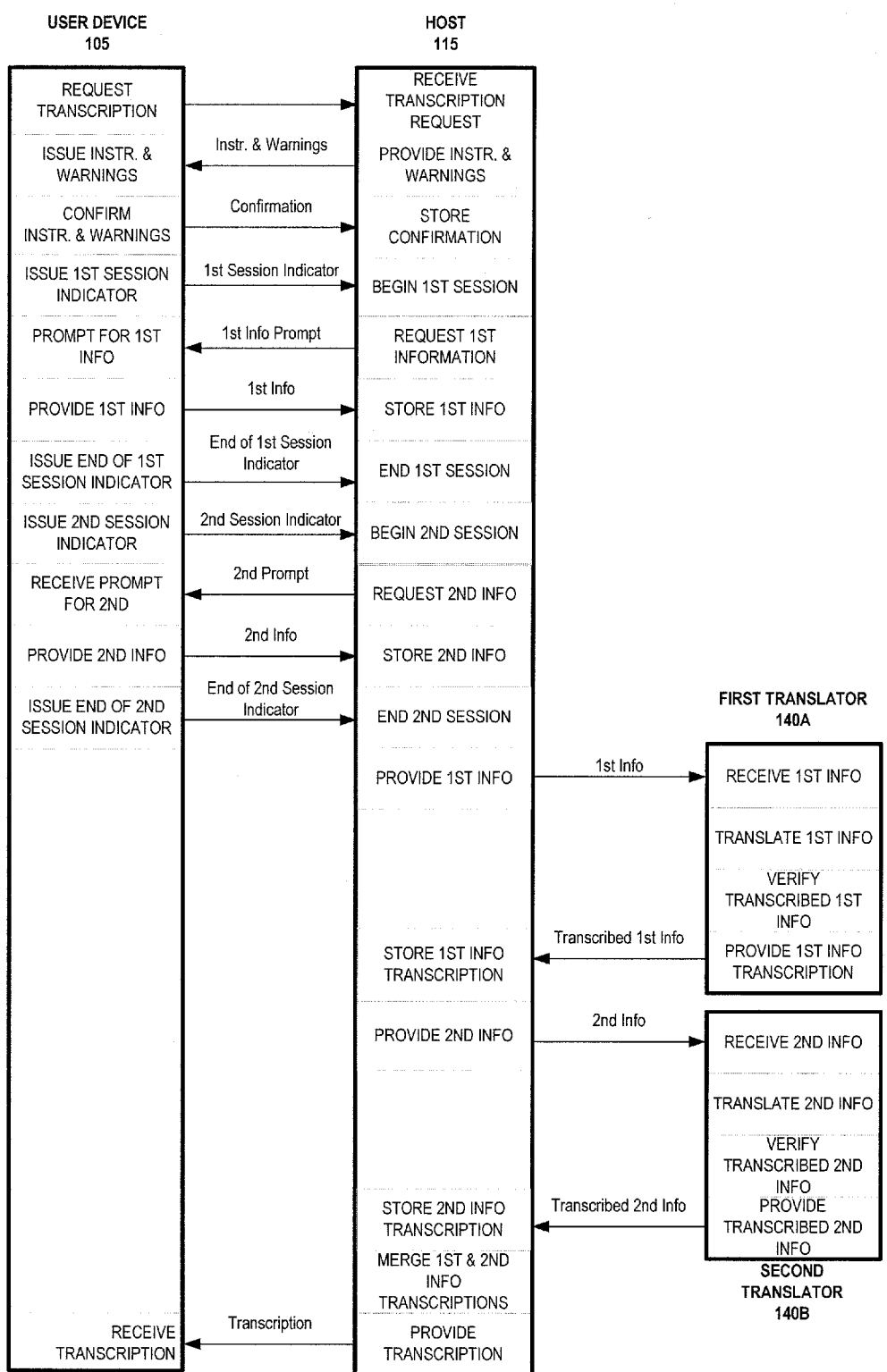
FIG. 2 is a time-flow diagram illustrating an exemplary method as disclosed herein.

FIG. 2 illustrates an exemplary time flow diagram, consistent with exemplary embodiments disclosed herein. Host 115 can receive a transaction request from user 110 and initiate a transcription. The initiation can include execution of transcription application 123 which can provide instructions, warnings, and prompts to user 110 to enter information segments. Transcription application 123 can also receive and store information provided by user 110 in data storage device 125. It can be required, for example, that user 110 acknowledges or confirms receipt and/or understanding of the instructions and warnings before dictating information to host 115. User 110's confirmation can be stored in data storage device 125 in association with the stored information segments A & B and their transcriptions.

Transcription application 123 can begin a first session to record a first information segment A that can include private information. Transcription application 123 can prompt user 110 to provide first information for information segment A that is collected only during the first session. For instance, transcription application 123 can prompt user 110 to provide header information segment for a medical report. The header information can include protected health information, for instance, about a patient whose exam results a health care provider wants transcribed.

Once user 110 completes entry of first information segment A, transcription application 123 can end the first session. For instance, when user 110 finishes speaking the header information segment, user 110 can press a key on the data entry device (e.g., telephone, computer or handheld recorder) to signal completion of the segment. Or, in a structured data entry system having several distinct data collection fields, transcription application 123 can end first session after entry of a last field.

After the first session ends, transcription application 123 can begin the second, separate session to collect second information for information segment B. For instance, transcription application 123 can prompt user 110 to provide the body of a medical report including only non-private information. As above, once user 110 completes entry of the second information segment B, host 115 may end the first session, for example, in response to an indication from user 110.

Host 115 can provide the first information segment A to a first transcriber 140A. For example, a health care provider may provide header information segment for an examination report to the host 115. The header information segment may include, for example, private health information of a patient. The host 115 may include a voice recognition unit that converts the dictation provided by the health care provider into and XML data file including tags classifying different portions of the data into classes, such as patient name, patient's age, sex, etc. Using the tags, first transcriber 140A may create a database record for the report.

Transcription application 123 can provide the second information segment B to the transcriber 140B. For example, a health care provider may provide body information of the examination report to host 115. Host 115 can be an individual or speech-to-text system that transcribes the spoken dictation provided by the health care provider into a text file. Consistent with exemplary embodiments disclosed herein, neither the information segment B nor the transcribed information in text file $B_t$ produced there from includes protected health information. Moreover, translators 140A & 140B do not share information included in information segment A and information segment B.

Transcription application 123 can retrieve information transcribed from segments A & B from text files $A_t$ & $B_t$, and combine the information into a single document. Host 115 can then provide the combined document to the user 110 or authorized recipient 150.

Figure 3:
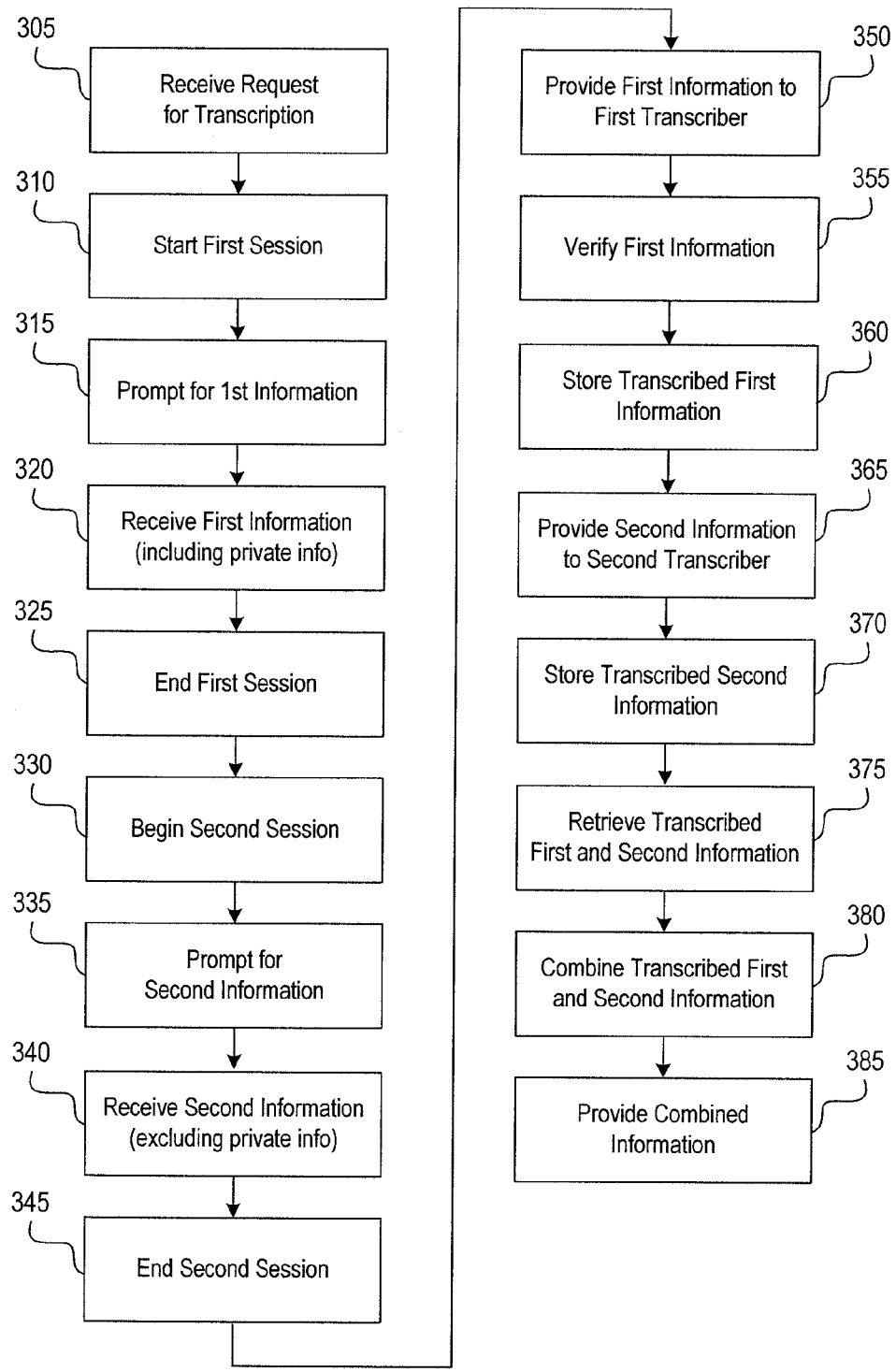
FIG. 3 is a flowchart diagram illustrating an exemplary method as disclosed herein.

FIG. 3 illustrates a flowchart diagram illustrating a method for transcribing information. Host 115 can receive a request for transcription from user 110. (Step 305.) Host 115 can then execute transcription application 123 to carry out the transcription process. Before it receives or requests any information, transcription application 123 can provide instructions, warnings and prompts to user 110. For instance, transcription application can provide a video or aural presentation explaining that the transcription will occur in two sessions and that any private information should only be provided during the first session.

Transcription application 123 can begin a first session to record first information segment A. (Step 310) At the outset of the first session, transcription application 123 can prompt user 110 to provide first information corresponding, for example, to the header of a document, including any private information. (Step 315.) During the first session user 110 provides the information for information segment A which is received by host 115. (Step 320.)

Once user 110 is finished providing information segment A, transcription application 123 ends the first session. (Step 325.) The first session can end after a predetermined amount of time, or user 110 can provide an indication to host 115 to end the first session. Alternatively, where information segment A is received as structured data, the session can end after user 110 provides the last information entry. At the end of the first session, transcription application 123 stores first information segment A in, for example, segment database 127. In the event, user 110 fails to indicate properly, the end of the first session, a trusted user will be engaged to separate the dictation into two segments A & B—one with private information and one without.

After the first session is completed, transcription application 123 begins the second session. (Step 330.) During the second session, transcription application 123 can prompt user 110 to provide second information corresponding, for example, to the body of a document. (Step 335.) Host 115 receives second information segment, which includes only non-private information. (Step 340.) Once user is finished providing information segment B, transcription application 123 ends the second session. (Step 345.) As with the first session, the second session can be ended, for example, after a predetermined amount of time, a user's indication, or after the last in a series of structured data entries is received. At the end of the second session, transcription application 123 can store information segment B in, for example, segment database 127.

Concurrently or subsequently with receiving information segments A & B, the information segments can be stored along with information associating the respective information segments A & B together. For instance, host 115, via transcription application 123 may store information segments in segment database 127 within data storage device 125, and information associating information segments A & B may be stored in segment linking table 129. To protect private information from unauthorized disclosure, only certain trusted individuals may have access to the information in segment linking table 129 and/or segment database 127.

Transcription application 123 provides information segment A to first 140A. (Step 350.) For instance, transcription application 123 can stream information segment A over communication channel 112. Once transcribed, first translator 140A can review translated first information segment $A_t$ to correct, for example, any errors and omissions. (Step 355.) Translated information of segment A included in text file $A_t$ can be stored at host 115 in segment database 127, for example. (Step 360.) Likewise, transcription application 123 provides information segment B to transcriber 140B. (Step 365.) Translated information segment $B_t$ can be stored at host 115 in segment database 127, for example. (Step 370.) In some embodiments, information segment A is only provided to an automated transcription system in order to ensure that private information is not disclosed to an individual.

Transcription application 123 can retrieve the transcribed information segments $A_t$ & $B_t$ based on information included in segment linking table 129 (step 375), and combine the transcribed information (step 380). Transcription application 123 can provide the combined translated information segments to user 110 or another recipient 150 authorized to receive the private information. (Step 385.)

As disclosed herein, embodiments and features of the invention can be implemented through computer hardware and/or software. Such embodiments can be implemented in various environments, such as networked and computing-based environments with one or more users. The present invention, however, is not limited to such examples, and embodiments of the invention can be implemented with other platforms and in other environments.

Moreover, while illustrative embodiments of the invention have been described herein, further embodiments can include equivalent elements, modifications, omissions, combinations (e.g., of aspects across various embodiments), adaptations and/or alterations as would be appreciated by those in the art based on the present disclosure.

Other embodiments of the invention will be apparent to those skilled in the art from consideration of the specification and practice of the embodiments of the invention disclosed herein. Further, the steps of the disclosed methods can be modified in various manners, including by reordering steps, executing multiple steps concurrently, and/or inserting or deleting steps, without departing from the principles of the invention. For instance, the description of separate data segments A and B could be altered to combine the segments into a single file with appropriate indexing and control of access to each segment, creating virtually separate files instead of physically separate files. It is therefore intended that the specification and embodiments be considered as exemplary only.

What is claimed is:

1. A method for transcribing information, comprising:
    receiving a first information segment during a first interview session, the first information segment including private information;
    receiving a second information segment during a second interview session, the second information segment including only non-private information;
    providing information included in the first information segment to a first transcriber;
    providing information included in the second information segment to a second transcriber;
    receiving a transcription of the information provided in the first information segment;
    receiving a transcription of the information provided in the second information segment; and
    providing a combination of the transcribed information in the first information segment and the transcribed information in the second information segment to a recipient authorized to receive the private information,
    wherein the first transcriber and the second transcriber do not communicate information from the first segment or the second segment to one another.

2. The method of claim 1, wherein:
    receiving the first information segment includes prompting a user to provide information including private information; and
    receiving the second information segment includes prompting the user to provide information excluding private information.

3. The method of claim 1, wherein providing information included in the first information segment, includes:
    providing the private information only to an automated transcription system.

4. The method of claim 1, wherein providing a combination includes:
    generating a document including the information transcribed from the first information segment and the information transcribed from the second information segment.

5. The method of claim 1, wherein the first information segment and the second information segment include audio data.

6. The method of claim 1, wherein the private information is protected health information.

7. A method for transcribing information, comprising:
    providing a first information segment during a first interview session, the first information segment including private information;
    providing a second information segment during a second interview session, the second information segment including only non-private information segment; and
    receiving a combination including the transcribed information in the first information segment and the transcribed information in the second information segment, wherein:
        the transcription of the information provided in the first information segment is provided by a first transcriber,
        the transcription of the information provided in the second information segment is provided by a second transcriber, and
        the first transcriber and the second transcriber do not communicate information from the first segment or the second segment to one another.

8. A method of claim 7, wherein:
    receiving the first information segment includes prompting a user to provide information segment including private information; and
    receiving the second information segment includes prompting the user to provide information segment excluding private information.

9. The method of claim 7, wherein providing information included in the first information segment, includes:
    providing the private information only to an automated transcription system.

10. The method of claim 7, wherein providing a combination includes:
    generating a document including the information transcribed from the first information segment and the information transcribed from in the second information segment.

11. The method of claim 7, wherein the first information segment and the second information segment include audio data.

12. The method of claim 7, wherein the private information is protected health information.

13. A system for transcribing of information, comprising:
    a processor; and
    a computer-readable medium including instructions that, when executed by the processor perform a method, the method including:
        receiving a first information segment during a first interview session, the first information segment including private information,
        receiving a second information segment during a second interview session, the second information segment including only non-private information,
        providing information included in the first information segment to a first transcriber,
        providing information included in the second information segment to a second transcriber;
        receiving a transcription of the information provided in the first information segment,
        receiving a transcription of the information provided in the second information segment, and
        providing a combination of the transcribed information in the first information segment and the transcribed information in the second information segment to a user authorized to receive the private information,
    wherein the first transcriber and the second transcriber do not communicate information from the first segment or the second segment to one another.

14. The method of claim 13, wherein providing information included in the first information segment, includes:

providing the private information only to an automated transcription system.

15. The system of claim 13, wherein providing a combination includes:
generating a document including the information transcribed from the first information segment and the information transcribed from the second information segment.

16. The system of claim 13, wherein the first information segment and the second information segment include audio data.

17. The system of claim 13, wherein the private information is protected health information.

\* \* \* \* \*

UNITED STATES PATENT AND TRADEMARK OFFICE
CERTIFICATE OF CORRECTION

| | |
|---|---|
| PATENT NO. | : 7,383,183 B1 |
| APPLICATION NO. | : 11/860902 |
| DATED | : June 3, 2008 |
| INVENTOR(S) | : Tad Alan Davis et al. |

Page 1 of 1

It is certified that error appears in the above-identified patent and that said Letters Patent is hereby corrected as shown below:

Column 10, Claim 14, line 1, change "method" to --system--.

Signed and Sealed this

Twenty-first Day of July, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,383,183 B1  Page 1 of 1
APPLICATION NO. : 11/860902
DATED : June 3, 2008
INVENTOR(S) : Tad Alan Davis et al.

It is certified that error appears in the above-identified patent and that said Letters Patent is hereby corrected as shown below:

Column 10, Claim 14, line 66, change "method" to --system--.

This certificate supersedes the Certificate of Correction issued July 21, 2009.

Signed and Sealed this

Eighteenth Day of August, 2009

David J. Kappos
*Director of the United States Patent and Trademark Office*